(12) United States Patent
Vaccarello

(10) Patent No.: US 11,001,553 B1
(45) Date of Patent: May 11, 2021

(54) PROCESS FOR THE SYNTHESIS OF 2-NITRATOETHYL ACRYLATE (2NEA)

(71) Applicant: The United States of America as Represented by the Secretary of the Navy, Indian Head, MD (US)

(72) Inventor: David N. Vaccarello, Laurel, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 16/974,149

(22) Filed: Oct. 22, 2020

(51) Int. Cl.
*C07C 201/08* (2006.01)
*C07C 201/16* (2006.01)
*C07C 205/49* (2006.01)

(52) U.S. Cl.
CPC .......... *C07C 201/08* (2013.01); *C07C 201/16* (2013.01); *C07C 205/49* (2013.01)

(58) Field of Classification Search
CPC .... C07C 201/08; C07C 201/16; C07C 205/49
See application file for complete search history.

(56) References Cited

U.S. PATENT DOCUMENTS

| 3,179,644 A | 4/1965 | Lawrence et al. |
| 8,658,818 B2 | 2/2014 | Stressler et al. |

OTHER PUBLICATIONS https://www.bing.com/search?q=ethylene+dinitrate&form=HPDTDF&pc=EUPP_HPDTDF&src=IE-SearchBox Pure Ethylene Glycol Dinitrate (EGDN) was first produced by the Belgian chemist Louis Henry (1834-1913) in 1870 by dropping a small amount of ethylene glycol into a mixture of nitric and sulfuric acids cooled to 0 C.
https://pubs.acs.org/doi/abs/10.1021/ja01167a527 N.S. Marans, and R.P. Zelinski Cite this: J. Am. Chem. Soc. 1950, 72, 11, 5330-5331 Publication Date: Nov. 1, 1950. The title of the citation is "2-Nitratoethyl Esters of Acrylic, Crotonic and Methacrylic Acids".

*Primary Examiner* — Jafar F Parsa
(74) *Attorney, Agent, or Firm* — Fredric J. Zimmerman

(57) ABSTRACT

An elegant process for the synthesis of 2-nitratoethyl acrylate is a single reactive step. A 2-hydroxyethyl acrylate having only one hydroxyl group is nitrated in a 1:1 volumetric mixture of nitric acid and sulfuric acid therein forming 2-nitratoethyl acrylate. The 2-nitratoethyl acrylate is minimally soluble in a quenched cold acid water mixture, which enables relatively easy isolation of about 96% purity 2-nitratoethyl acrylate at a yield of about 85%.

3 Claims, 1 Drawing Sheet

Process for the Synthesis of 2-nitratoethyl acrylate (2NEA)

Process for the Synthesis of 2-nitratoethyl acrylate (2NEA)
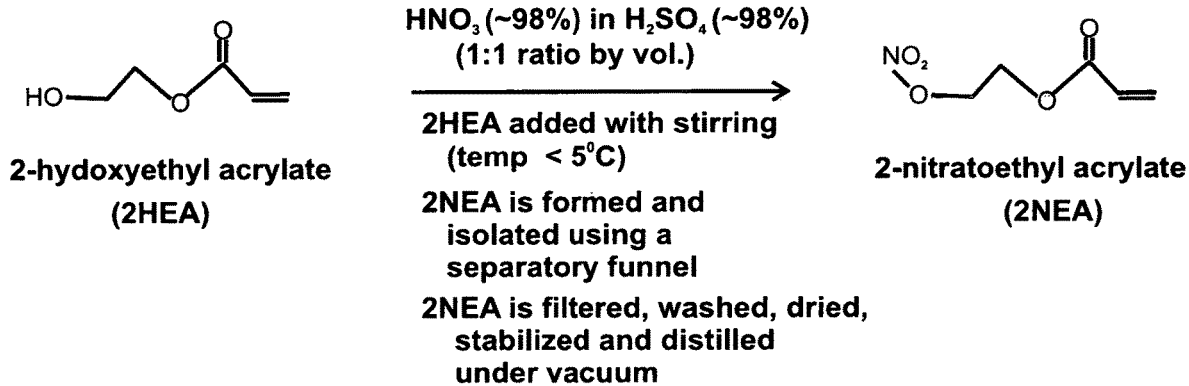

PROCESS FOR THE SYNTHESIS OF 2-NITRATOETHYL ACRYLATE (2NEA)

STATEMENT OF GOVERNMENT INTEREST

The invention described herein may be manufactured and used by or for the Government of the United States of America for Governmental purposes without the payment of any royalties thereon or therefore.

FIELD OF THE INVENTION

The present invention relates generally to the synthesis of 2-nitratoethyl acrylate. More particularly, the present invention is a new process for the synthesis of 2-nitratoethyl acrylate, wherein the new process has fewer steps, utilizes inexpensive commercially available starting materials, provides for a significantly higher yield, and reduces an incidental presence or accidental formation of Ethylene Glycol Dinitrate (EGDN) and hydrogen chloride.

BACKGROUND OF THE INVENTION

Nitration has been around since before Alfred Nobel. One of the first documented examples was the synthesis of Ethylene Glycol Dinitrate (EGDN), which was synthesized in 1870 by Belgian chemist Louis Henry. EGDN was formed by dropping a small amount of ethylene glycol into a mixture of nitric and sulfuric acid, therein converting each of the hydroxyl groups into a nitrato group. Nitroglycerine was made using a similar process, except with glycerin.

Straessler et al in U.S. Pat. No. 8,658,818 teach a process for forming poly nitrate esters of aliphatic di, tri, and tetra polyols using a mixture of sulfuric acid, ammonium nitrate and a metal nitrate.

Joseph W. Lawrence and Harold F. Bluhm teach in U.S. Pat. No. 3,179,644 that 2-nitratoethyl acrylate can be formed by reacting β-nitratoethanol with acrylyl chloride. A reaction by-product is hydrogen chloride which hydrates to hydrochloric acid. The β-nitratoethanol (a.k.a. 2-nitratoethanol) can reputedly be made by reacting ethylene oxide with nitric acid forming mono-nitratoethanol and di-nitratoethane (a.k.a. mono-nitroglycol and di-nitroglycol) according to Orlova, E Y (1981), Chemistry and technology of high explosives: Textbook for high schools (3 ed.); Khimiya. p. 278. Note, dinitroglycol is another name for ethylene glycol dinitrate (Louis Henry's EGDN). EGDN is one the first known aliphatic nitrate explosives, and it is sensitive to heat and shock. Lastly, these conventional generally two-step processes, which use commercial starting materials, have an overall yield of between about 21-42% (percent).

SUMMARY OF THE INVENTION

The invention is a new process for the synthesis of 2-nitratoethyl acrylate.

An aspect of the invented process is it reduces an incidental presence or accidental formation of EGDN, as the synthesis employs 2-hydroxyethyl acrylate, which has only one hydroxyl group that can be nitrated. This benefit is in contrast to reacting β-nitratoethanol with acrylyl chloride, wherein, in addition to β-nitratoethanol, the undesired dinitratoethanol (EGDN) explosive also may be formed.

A second aspect of the invented process is that there is no formation of hydrogen chloride or hydrochloric acid.

A third aspect of the invented process is that 2-hydroxyethyl acrylate is commercially available. For example Sigma Aldrich sells 2-hydroxyethyl acrylate for 3 cents/gram and in bulk (for example 1 ton) for ~$50/lb.

A fourth aspect of the invented process is that 2-nitratoethyl acrylate may be separated from the nitrating acid mixture of nitric acid and sulfuric acid by simple phase separation. This phase separation potentially enables the nitrating acid mixture to be used again following treatment to remove most of the water that is added or is formed. Overall, this reaction is generally a two-phase reaction.

A final aspect of the invention is that the process for the synthesis of 2-nitratoethyl acrylate is a single reactive step, wherein 2-hydroxyethyl acrylate has only one hydroxyl group that may be nitrated therein forming the 2-nitratoethyl acrylate, and that the 2-nitratoethyl acrylate is minimally soluble in a cold acid water mixture. The resultant yield is about 85% after distillation, which is significantly higher than conventional methods.

BRIEF DESCRIPTION OF THE DRAWINGS

The foregoing invention will become readily apparent by referring to the following detailed description and the appended drawing in which:

FIG. 1 illustrates the starting material (2HEA), the reagents nitric acid in sulfuric acid, and the purification processes (separation, filtering, washing, drying, vacuum distillation); therein synthesizing in high yield and in high purity the desired product (2NEA).

DETAILED DESCRIPTION OF THE INVENTION

The invented new and elegant process is the synthesis of 2-nitratoethyl acrylate.

Actual Synthesis. A lab size synthesis is described herein. The process utilized commercially available 2-hydroxyethyl acrylate ($0.03/g, Sigma-Aldrich). The nitrating acid mixture was 98% $H_2SO_4$ and 98% $HNO_3$, wherein the nitrating acid mixture was formed by carefully mixing the acids in a 1:1 volume ratio in a test tube and cooled to 0° C. in an ice bath. The 2-hydroxyethyl acrylate (2HEA) was added slow enough to maintain the temperature below 5° C., while being vigorously stirring using a magnetic stirrer. After the addition of 2HEA is complete, ice may be added to quench the excess acid. Stirring was halted and the contents of the test tube were transferred to a separatory funnel. The product (2NEA) is in an upper phase, and it was separated from the quenched excess acid, which in a lower acid phase. The product was collected by draining off the lower phase. The product was dried over sodium sulfate and filtered. The formed sodium sulfate filter cake was washed with dichloromethane (DCM). A small quantity of BHT (butylated hydroxytoluene—which is a common free radical inhibitor) was added to the product that is now dissolved in the DCM. The dissolved product with BHT was then concentrated by rotary evaporation and the concentrated product was purified by vacuum distillation, for example using spinning band distillation (115° C. at 100 millitorr). Another small quantity of BHT was added to the purified product. The yield after distillation is 85%. Again, this yield is significantly higher than the conventional technology processes as previously discussed.

The product was unambiguously characterized as 2-nitratoethyl acrylate as determined by $^1H$, $^{13}C$ NMR, and DART-MS: calculated for $C_5H_8NO_5$ $[M+H]^+=162.0402$, found at 162.0407. GC/FID (Gas Chromatography using a Flame Ionization Detector) analysis, determined the purity to be 96%. The product is of high purity and is acceptable for subsequent uses, such as polymerization via the acrylate moiety, into poly-2-nitratoethyl acrylate.

As stated the yield following distillation is high yield and the purity is excellent. The separation of the crude 2-nitratoethyl acrylate from the icy aqueous acid phase was very nearly 100% in order to achieve such a high yield.

Potentially, all or part of the acid phase may be reused following drying and/or distillation to remove the water. Nitric acid forms an azeotrope with water during distillation. Additional nitric acid may be added to compensate for the nitric acid consumed by the synthesis and the distillation.

FIG. 1 illustrates the synthesis of 2NEA from 2HEA. 2NEA and 2HEA are only minimally soluble in water, and likewise water is only minimally soluble in 2NEA and 2HEA, so the reaction is largely a two phase reaction, hence the need for rapid stirring.

The actual process for the synthesis of 2-nitratoethyl acrylate includes the following: adding, in fractional molar increments, a reagent amount of 2-hydroxyethyl acrylate to a stirred cooled mixture that has a molar excess of concentrated nitric acid combined with a comparable volume of concentrated sulfuric acid. The fractional molar increments are small enough that the temperature of the stirred cooled mixture was below 5° C. temperature. Following complete addition of the reagent amount of 2-hydroxyethyl acrylate, the stirred cooled mixture was quenched, typically with ice and/or icy water. Stirring was stopped, and the cooled mixture phase separated into an upper layer that is principally 2-nitratoethyl acrylate, and a lower layer that is principally concentrated nitric acid and concentrated sulfuric acid.

In the next step the upper layer was separated from the lower layer, wherein the upper layer has a molar yield that is greater than 85% of the reagent amount of 2-hydroxyethyl acrylate.

Further drying and purification was next, as well as stabilization of the acrylate to prevent polymerization, by the addition of free radical inhibitors, like BHT. Following distillation, the yield of 2-nitratoethyl acrylate was about 85%, where the 2-nitratoethyl acrylate is 96% pure.

Nitrate esters may be converted in the body to nitric oxide, a potent natural vasodilator. In medicine, these esters are used as a medicine for angina pectoris (ischemic heart disease). It is anticipated that 2NEA and derivatives thereof could have medicinal benefits.

Although the present disclosure has been illustrated and described herein with reference to exemplary embodiments and specific examples thereof, it will be readily apparent to those of ordinary skill in the art that other exemplary embodiments and examples may perform similar functions and/or achieve like results. All such equivalent embodiments and examples are within the spirit and scope of the present disclosure, are contemplated thereby, and are intended to be covered by the following claims.

Finally, any numerical parameters set forth in this Specification and the attached Claims are approximations (for example, by using the term "about") that may vary depending upon the desired properties sought to be obtained by the present invention. At the very least, and not as an attempt to limit the application of the doctrine of equivalents to the scope of the Claims, each numerical parameter should be construed in light of the number of significant digits and by applying ordinary rounding.

It is to be understood that the foregoing description and specific exemplary embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

What is claimed is:

1. A process for the synthesis of 2-nitratoethyl acrylate, comprising:
   adding, in fractional molar increments, a reagent amount of 2-hydroxyethyl acrylate to a stirred cooled mixture being comprised of a molar excess of concentrated nitric acid combined with a comparable volume of concentrated sulfuric acid,
   wherein the fractional molar increments are small enough that the temperature of the stirred cooled mixture is below a temperature of 5° C.;
   completing the adding of the reagent amount of 2-hydroxyethyl acrylate;
   quenching the stirred cooled mixture;
   stopping stirring, where upon a cooled mixture phase separates into an upper layer, which is principally comprised of 2-nitratoethyl acrylate, and a lower layer, which is principally comprised of concentrated nitric acid and concentrated sulfuric acid; and
   separating the upper layer from the lower layer, wherein the upper layer has a molar yield that is greater than 85% of the starting molar amount of 2-hydroxyethyl acrylate.

2. The process according to claim 1, further comprising:
   drying the upper layer dried over sodium sulfate forming a sodium sulfate filter cake;
   washing the sodium sulfate filter cake with dichloromethane (DCM);
   adding a small quantity of free radical inhibitor, wherein the free radical inhibitor is butylated hydroxytoluene (BHT);
   concentrating the 2-nitratoethyl acrylate using rotary evaporation to remove DCM; and
   distilling a concentrated 2-nitratoethyl acrylate by vacuum distillation, with a boiling point (bp) of −115° C. at 100 millitorr, wherein a distilled 2-nitratoethyl acrylate has a purity of about 96% and an overall yield of about 85%.

3. The process according to claim 1, further comprising:
   drying the upper layer dried over sodium sulfate forming a sodium sulfate filter cake;
   washing the sodium sulfate filter cake with dichloromethane (DCM);
   adding a small quantity of a free radical inhibitor, wherein the free radical inhibitor is butylated hydroxytoluene (BHT);
   concentrating the 2-nitratoethyl acrylate using rotary evaporation to remove DCM;
   distilling the concentrated 2-nitratoethyl acrylate by vacuum distillation, with a boiling point (bp) of −115° C. at 100 millitorr, wherein a distilled 2-nitratoethyl acrylate has a purity of about 96% and an overall yield of about 85%; and
   adding another small quantity of the free radical inhibitor.

* * * * *